US012327013B2

(12) United States Patent
Magliari et al.

(10) Patent No.: US 12,327,013 B2
(45) Date of Patent: Jun. 10, 2025

(54) GRAPHICAL USER INTERFACE CONTROL DEVICE FOR RADIATION THERAPY TREATMENT PLANNING

(71) Applicant: SIEMENS HEALTHINEERS INTERNATIONAL AG, Steinhausen (CH)

(72) Inventors: Anthony Magliari, Swansea, IL (US); Jessica Perez, Geneva (CH); Michael Folkerts, Carrollton, TX (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

(21) Appl. No.: 17/709,176

(22) Filed: Mar. 30, 2022

(65) Prior Publication Data
US 2023/0315272 A1    Oct. 5, 2023

(51) Int. Cl.
*G06F 3/04847*    (2022.01)
*A61N 5/10*    (2006.01)

(52) U.S. Cl.
CPC ......... *G06F 3/04847* (2013.01); *A61N 5/103* (2013.01); *A61N 5/1048* (2013.01); *A61N 2005/1074* (2013.01)

(58) Field of Classification Search
None
See application file for complete search history.

(56) References Cited

U.S. PATENT DOCUMENTS

| | | | | |
|---|---|---|---|---|
| 6,038,283 A * | 3/2000 | Carol | ................... | G16H 70/20 378/65 |
| 7,391,026 B2 * | 6/2008 | Trinkaus | ............... | G16H 70/20 378/65 |
| 10,092,774 B1 * | 10/2018 | Vanderstraten | ........ | G16H 10/60 |
| 10,583,310 B1 * | 3/2020 | Fram | ..................... | G16H 30/20 |
| 10,850,120 B2 * | 12/2020 | Laaksonen | .......... | A61N 5/1031 |
| 11,116,995 B2 * | 9/2021 | Khuntia | ............... | A61N 5/1031 |
| 2006/0274885 A1 | 12/2006 | Wang et al. | | |
| 2007/0203902 A1 * | 8/2007 | Bauerle | ................ | G06F 16/283 707/999.005 |
| 2010/0183121 A1 * | 7/2010 | Riker | .................... | G16H 70/20 378/65 |
| 2010/0228116 A1 * | 9/2010 | Lu | ......................... | A61N 5/103 703/11 |
| 2012/0136677 A1 * | 5/2012 | Ziegenhein | ........... | G16H 20/40 705/2 |
| 2013/0304503 A1 * | 11/2013 | Kuefer | ................. | A61N 5/1031 705/2 |

(Continued)

OTHER PUBLICATIONS

In re Nuijten, 500 F.3d 1346, 1356-57 (Fed. Cir. 2007).

(Continued)

*Primary Examiner* — William L Bashore
*Assistant Examiner* — Koorosh Nehchiri
(74) *Attorney, Agent, or Firm* — Harness, Dickey & Pierce, P.L.C.

(57) ABSTRACT

A graphical user interface is configured for display on a computer display. The graphical user interface includes a dose rate slider configured to enable a user to select a range of radiation dose rates of a radiotherapy plan, and a display image configured to present an image. The dose rate slider may be selectable among less than a value of the dose rate slider, and more than a value of the dose rate slider.

21 Claims, 12 Drawing Sheets

(56) References Cited

U.S. PATENT DOCUMENTS

| | | | |
|---|---|---|---|
| 2014/0275706 A1* | 9/2014 | Dean | A61N 5/1031 |
| | | | 600/1 |
| 2014/0337510 A1* | 11/2014 | Gesmann | G06F 11/3409 |
| | | | 709/224 |
| 2019/0083814 A1* | 3/2019 | Tallinen | A61N 5/1031 |
| 2020/0121957 A1 | 4/2020 | Fishman et al. | |
| 2020/0282232 A1* | 9/2020 | Khuntia | A61N 5/1031 |
| 2020/0286601 A1* | 9/2020 | Khuntia | G16H 15/00 |
| 2020/0384289 A1* | 12/2020 | Smith | A61N 5/1081 |
| 2021/0016108 A1* | 1/2021 | Khuntia | A61N 5/103 |
| 2021/0052916 A1 | 2/2021 | Isola | |
| 2021/0052917 A1* | 2/2021 | Vanderstraeten | G16H 20/40 |
| 2021/0392982 A1 | 12/2021 | Benja-Athon | |
| 2021/0393982 A1 | 12/2021 | Lansonneur et al. | |
| 2022/0126116 A1* | 4/2022 | Harrer | G16H 20/40 |
| 2023/0128148 A1* | 4/2023 | Li | A61N 5/1036 |
| | | | 600/1 |

OTHER PUBLICATIONS

IEEE Standard Microcomputer System Bus. New York, NY: IEEE, 1983.
IEEE Standard for a Simple 32-Bit Backplane Bus: NuBus. New York, NY: IEEE, 1988.
IEEE Standard for a Chip and Module Interconnect Bus : SBus. New York, NY: IEEE, 1993.
IEEE Standard for a High Performance Serial Bus : New York, NY: IEEE, 2008.

* cited by examiner

800

START

↓

810 DISPLAY A FIRST WINDOW COMPRISING GRAPHICAL INFORMATION OF THE RADIOTHERAPY PLAN IN A FIRST FORMAT WITHIN THE GUI ON A COMPUTER DISPLAY

↓

820 DISPLAY A SECOND WINDOW COMPRISING A DOSE RATE SLIDER CONFIGURED TO DISPLAY A RANGE OF DOSE RATES WITHIN THE GUI

↓

830 ACCEPTING USER INPUT VIA THE DOSE RATE SLIDER TO SELECT THE RANGE OF DOSE RATES

↓

840 AUTOMATICALLY UPDATE THE FIRST WINDOW TO DISPLAY RADIATION DOSAGE DELIVERED AT THE RANGE OF DOSE RATES

↓

850 PRECOMPUTE UPDATES TO THE FIRST WINDOW CORRESPONDING TO A PLURALITY OF DOSE RATE RANGES

↓

End

Fig. 8

GRAPHICAL USER INTERFACE CONTROL DEVICE FOR RADIATION THERAPY TREATMENT PLANNING

RELATED CASE(S)

The present application is related to U.S. Pat. No. 11,116,995, filed Mar. 6, 2019, U.S. Pat. No. 10,918,886, filed Jun. 10, 2019, and U.S. patent application Ser. No. 17/323,942, filed May 18, 2021. All such Applications and Patents are incorporated herein by reference in their entireties.

FIELD OF INVENTION

Embodiments of the present invention relate to the field of medical devices. More specifically, embodiments of the present invention relate to systems and methods for graphical user interface control devices for radiation therapy treatment planning.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

Before a patient is treated with radiation, a treatment plan specific to that patient is developed. The treatment plan defines various aspects of the therapy using simulations and optimizations that may be based on past experiences. In general, the purpose of the treatment plan is to deliver sufficient radiation to the unhealthy tissue while minimizing exposure of surrounding healthy tissue to the radiation.

The treatment planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find a plan that is best suited to achieving the desired outcome.

FLASH radiotherapy is an emerging radiotherapy regime that appears to reduce radiation-induced toxicities while maintaining a tumor response similar to that of more conventional radiotherapy regimes. This is sometimes known as or referred to as a "FLASH effect." FLASH radiotherapy may be characterized as delivering a high radiation rate, e.g., greater than about 40 Grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, FLASH radiotherapy may deliver a similar total dose at a rate of 40 Gy/s, requiring a fraction of a second of treatment time.

FLASH radiotherapy introduces important interdependencies that are not captured by conventional radiation treatment planning. Current tools such as dose-volume histograms and dose-rate volume histograms do not capture the interdependence of dose and dose rate. For example, developing a dose rate distribution for a high-quality plan is not trivial from a clinician's perspective because normal tissue might benefit from a low dose rate in certain regions if the dose is minimized in these regions. Also, for example, irradiating a restricted number of spots in a treatment volume may lead to high dose rate delivery but low dose homogeneity at the level of a tumor, while on the other hand, plan quality could be improved by increasing the number of spots at the cost of lowering the dose rate. Further, conventional types of information displays may not provide sufficient information for a clinician to understand many of the characteristics of a FLASH radiotherapy treatment plan.

SUMMARY OF THE INVENTION

Therefore, what is needed are systems and methods for graphical user interface control devices for radiation therapy treatment planning. What is additionally needed are systems and methods for graphical user interface control devices for radiation therapy treatment planning that display dosage information based on a user selected dose rate. There is a further need for systems and methods for graphical user interface control devices for radiation therapy treatment planning that are compatible and complementary with existing systems and methods of planning and/or administering radiotherapy.

In accordance with a first embodiment of the present invention, a graphical user interface is configured for display on a computer display. The graphical user interface includes a dose rate slider configured to enable a user to select a range of radiation dose rates of a radiotherapy plan, and a display image configured to present an image. The dose rate slider may be selectable among less than a value of the dose rate slider, and more than a value of the dose rate slider.

In accordance with a method embodiment, a computer-implemented method for dynamically updating displays of radiotherapy plan information in a graphical user interface (GUI) includes displaying a first window comprising graphical information of the radiotherapy plan in a first format within the GUI on a computer display, displaying a second window comprising a dose rate slider configured to display a range of dose rates within the GUI, accepting user input via the dose rate slider to select the range of dose rates, and automatically updating the first window to display radiation dosage delivered at the range of dose rates. The method may also include precomputing updates to the first window corresponding to a plurality of dose rate ranges.

In accordance with another embodiment of the present invention, a non-transitory computer-readable storage medium having computer-executable instructions for causing a computer system to perform a method for dynamically updating displays of radiotherapy plan information in a graphical user interface (GUI). The method includes displaying a first window comprising graphical information of the radiotherapy plan in a first format within the GUI on a computer display, displaying a second window comprising a dose rate slider configured to display a range of dose rates within the GUI, accepting user input via the dose rate slider to select the range of dose rates, and automatically updating the first window to display radiation dosage delivered at the range of dose rates. The method may also include precomputing updates to the first window corresponding to a plurality of dose rate ranges.

BRIEF DESCRIPTION OF THE DRAWINGS

The accompanying drawings, which are incorporated in and form a part of this specification, illustrate embodiments of the invention and, together with the description, serve to explain the principles of the invention. Unless otherwise noted, the drawings may not be drawn to scale.

FIG. 8 is a flow chart of an exemplary computer-implemented method for dynamically updating displays of radiotherapy plan information in a graphical user interface.

DETAILED DESCRIPTION

Figure 1:
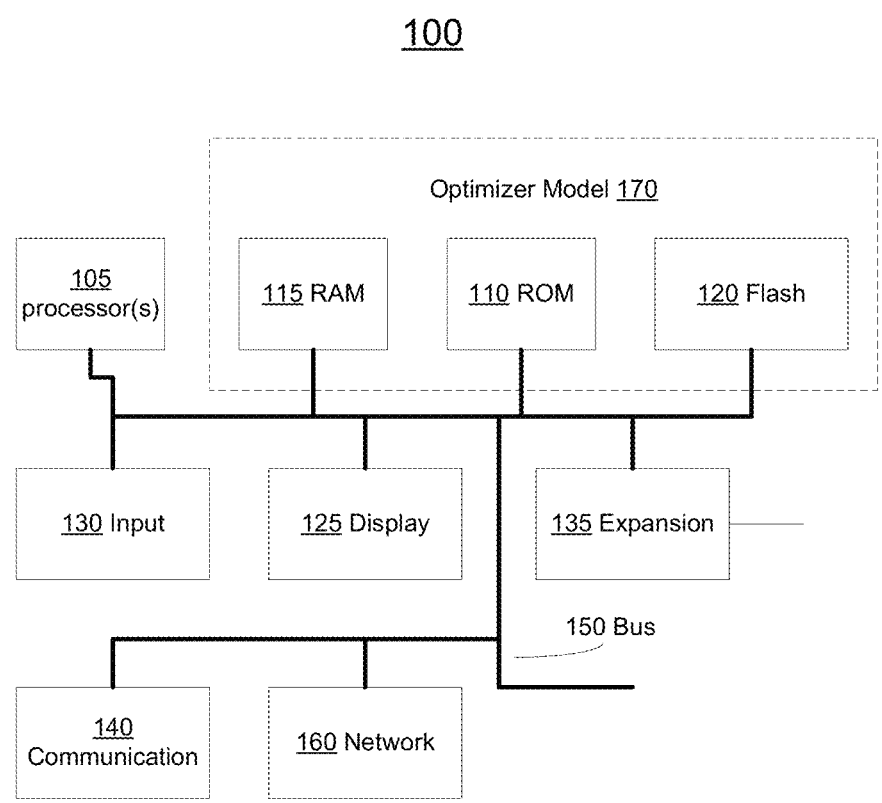
FIG. 1 illustrates a block diagram of an exemplary electronic system, which may be used as a platform to implement and/or as a control system for embodiments of the present invention.

Reference will now be made in detail to various embodiments of the invention, examples of which are illustrated in the accompanying drawings. While the invention will be described in conjunction with these embodiments, it is understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the invention, numerous specific details are set forth in order to provide a thorough understanding of the invention. However, it will be recognized by one of ordinary skill in the art that the invention may be practiced without these specific details. In other instances, well known methods, procedures, components, and circuits have not been described in detail as not to unnecessarily obscure aspects of the invention.

Some portions of the detailed descriptions which follow (e.g., method 800) are presented in terms of procedures, steps, logic blocks, processing, and other symbolic representations of operations on data bits that may be performed on computer memory. These descriptions and representations are the means used by those skilled in the data processing arts to most effectively convey the substance of their work to others skilled in the art. A procedure, computer executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, data, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "applying" or "controlling" or "generating" or "testing" or "heating" or "bringing" or "capturing" or "storing" or "reading" or "analyzing" or "resolving" or "accepting" or "selecting" or "determining" or "displaying" or "presenting" or "computing" or "sending" or "receiving" or "reducing" or "detecting" or "setting" or "accessing" or "placing" or "forming" or "mounting" or "removing" or "ceasing" or "stopping" or "coating" or "processing" or "performing" or "adjusting" or "creating" or "executing" or "continuing" or "indexing" or "translating" or "calculating" or "measuring" or "gathering" or "running" or the like, refer to the action and processes of, or under the control of, a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The meaning of "non-transitory computer-readable medium" should be construed to exclude only those types of transitory computer-readable media which were found to fall outside the scope of patentable subject matter under 35 U.S.C. § 101 in In re Nuijten, 500 F.3d 1346, 1356-57 (Fed. Cir. 2007). The use of this term is to be understood to remove only propagating transitory signals per se from the claim scope and does not relinquish rights to all standard computer-readable media that are not only propagating transitory signals per se.

In the following descriptions, various elements and/or features of embodiments in accordance with the present invention are presented in isolation so as to better illustrate such features and as not to unnecessarily obscure aspects of the invention. It is to be appreciated, however, that such features, e.g., as disclosed with respect to a first drawing, may be combined with other features disclosed in other drawings in a variety of combinations. All such embodiments are anticipated and considered, and may represent embodiments in accordance with the present invention.

Graphical User Interface Control Device for Radiation Therapy Treatment Planning FIG. 1 illustrates a block diagram of an exemplary electronic system 100, which may be used as a platform to plan radiation treatments, implement radiation treatments, and/or as a control system for a radiation treatment system. Exemplary radiation systems may be similar to a ProBeam® 360° radiotherapy system or a TrueBeam® radiotherapy system, both of which are commercially available from Varian Medical Systems, Palo Alto, CA. Embodiments in accordance with the present invention are applicable to any type of radiation, including, for example, light ion particles such as protons, alpha particles, or carbon ions, X-rays, and/or electrons, arising from cyclotrons, linear accelerators, and/or other sources.

Electronic system 100 may be a "server" computer system, in some embodiments. Electronic system 100 includes an address/data bus 150 for communicating information, a central processor complex 105 functionally coupled with the bus for processing information and instructions. Bus 150 may comprise, for example, a Peripheral Component Interconnect Express (PCIe) computer expansion bus, industry standard architecture (ISA), extended ISA (EISA), Micro-Channel, Multibus, IEEE 796, IEEE 1196, IEEE 1496, PCI, Computer Automated Measurement and Control (CAMAC), MBus, Runway bus, Compute Express Link (CXL), and the like.

Central processor complex 105 may comprise a single processor or multiple processors, e.g., a multi-core processor, or multiple separate processors, in some embodiments. Central processor complex 105 may comprise various types of well-known processors in any combination, including, for example, digital signal processors (DSP), graphics processors (GPU), complex instruction set (CISC) processors, reduced instruction set (RISC) processors, and/or very long word instruction set (VLIW) processors. In some embodiments, exemplary central processor complex 105 may comprise a finite state machine, for example, realized in one or more field programmable gate array(s) (FPGA), which may operate in conjunction with and/or replace other types of processors to control embodiments in accordance with the present invention.

Electronic system 100 may also include a volatile memory 115 (e.g., random access memory RAM) coupled with the bus 150 for storing information and instructions for the central processor complex 105, and a non-volatile memory 110 (e.g., read only memory ROM) coupled with the bus 150 for storing static information and instructions for the processor complex 105. Electronic system 100 also optionally includes a changeable, non-volatile memory 120 (e.g., NOR flash) for storing information and instructions for the central processor complex 105 which can be updated after the manufacture of system 100. In some embodiments, only one of ROM 110 and/or Flash memory 120 may be present.

Also included in electronic system 100 of FIG. 1 is an optional input device 130. Input device 130 can communicate information and command selections to the central processor complex 105. Input device 130 may be any suitable device for communicating information and/or commands to the electronic system 100. For example, input device 130 may take the form of a keyboard, buttons, a joystick, a track ball, an audio transducer, e.g., a microphone, a touch sensitive digitizer panel, eyeball scanner, and/or the like.

Electronic system 100 may comprise a display unit 125. Display unit 125 may comprise a liquid crystal display (LCD) device, cathode ray tube (CRT), field emission device (FED, also called flat panel CRT), light emitting diode (LED), plasma display device, electro-luminescent display, electronic paper, electronic ink (e-ink) or other display device suitable for creating graphic images and/or alphanumeric characters recognizable to the user. Display unit 125 may have an associated lighting device, in some embodiments.

Electronic system 100 also optionally includes an expansion interface 135 coupled with the bus 150. Expansion interface 135 can implement many well known standard expansion interfaces, including without limitation the Secure Digital Card interface, universal serial bus (USB) interface, Compact Flash, Personal Computer (PC) Card interface, CardBus, Peripheral Component Interconnect (PCI) interface, Peripheral Component Interconnect Express (PCI Express), mini-PCI interface, IEEE 1394, Small Computer System Interface (SCSI), Personal Computer Memory Card International Association (PCMCIA) interface, Industry Standard Architecture (ISA) interface, RS-232 interface, and/or the like. In some embodiments of the present invention, expansion interface 135 may comprise signals substantially compliant with the signals of bus 150.

A wide variety of well-known devices may be attached to electronic system 100 via the bus 150 and/or expansion interface 135. Examples of such devices include without limitation rotating magnetic memory devices, flash memory devices, digital cameras, wireless communication modules, digital audio players, and Global Positioning System (GPS) devices.

System 100 also optionally includes a communication port 140. Communication port 140 may be implemented as part of expansion interface 135. When implemented as a separate interface, communication port 140 may typically be used to exchange information with other devices via communication-oriented data transfer protocols. Examples of communication ports include without limitation RS-232 ports, universal asynchronous receiver transmitters (UARTs), USB ports, infrared light transceivers, ethernet ports, IEEE 1394, and synchronous ports.

System 100 optionally includes a network interface 160, which may implement a wired or wireless network interface. Electronic system 100 may comprise additional software and/or hardware features (not shown) in some embodiments.

Various modules of system 100 may access computer readable media, and the term is known or understood to include removable media, for example, Secure Digital ("SD") cards, CD and/or DVD ROMs, diskettes and the like, as well as non-removable or internal media, for example, hard drives, solid state drives (SSD), RAM, ROM, flash memory, and the like.

In the example of FIG. 1, the memory 115, 110, and/or 120 includes computer-readable instructions, data structures, program modules, and/or the like associated with an "optimizer" model 170. However, the optimizer model 170 may instead reside in any one of the computer storage media used by the system 100, or may be distributed over some combination of the computer storage media, or may be distributed over some combination of networked computers. The functionality of the optimizer model 170 is further described below.

Figure 2:
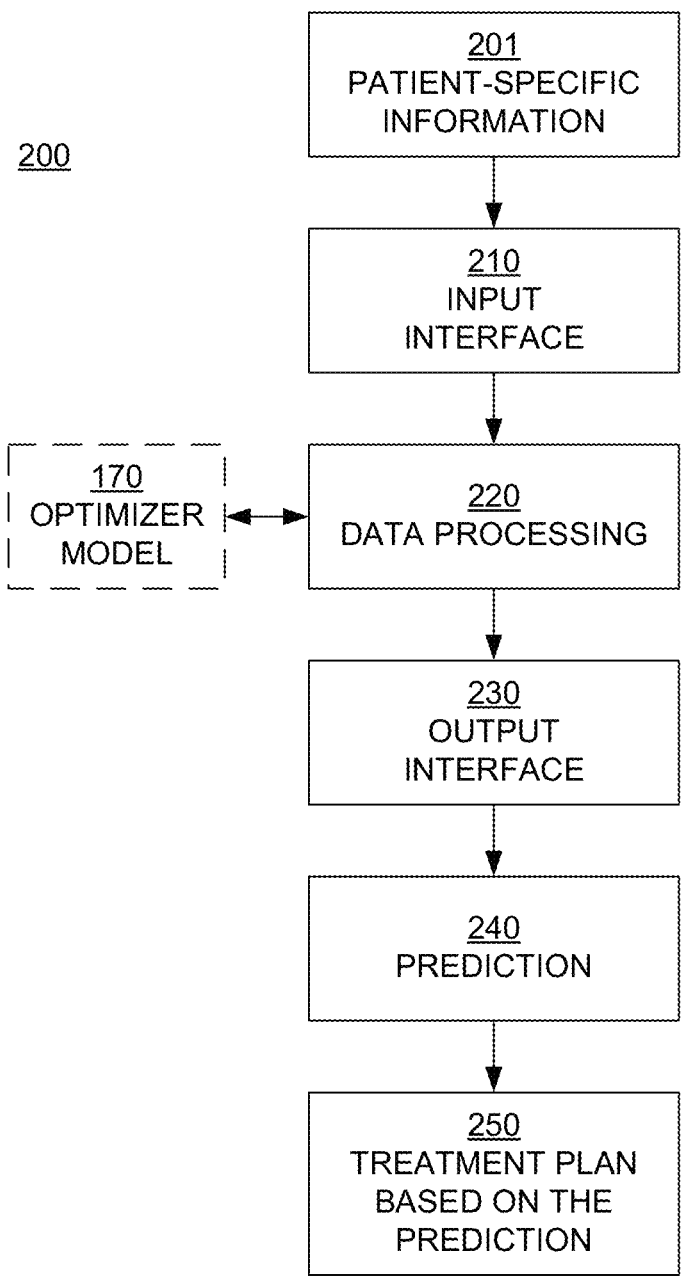
FIG. 2 is a block diagram illustrating an example of an automated radiation therapy treatment planning system, in accordance with embodiments of the present invention.

FIG. 2 is a block diagram illustrating an example of an automated radiation therapy treatment planning system 200, in accordance with embodiments of the present invention. The planning system 200 includes an input interface 210 to receive patient-specific information (data) 201, a data processing component 220 that implements the optimizer model 170 (FIG. 1), and an output interface 230. The planning system 200 in whole or in part may be implemented as a software program, hardware logic, or a combination thereof on and/or using the computer system 100 (FIG. 1).

In the example of FIG. 2, patient-specific information is provided to and processed by the optimizer model 170. In embodiments, the optimizer model 170 yields a prediction result 240, and a treatment plan 250 based on the prediction result can then be generated.

Figure 3:
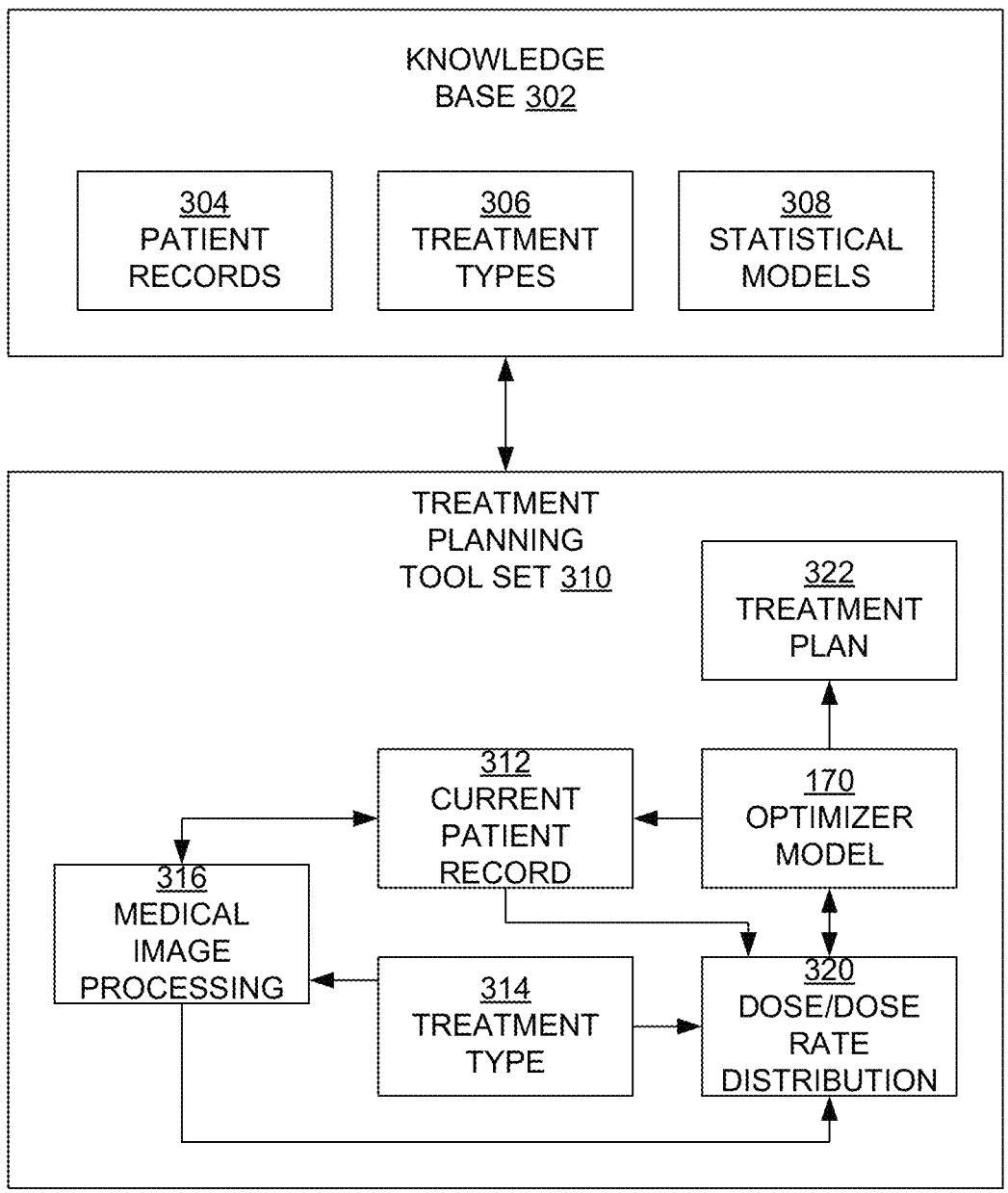
FIG. 3 illustrates an exemplary knowledge-based planning system, in accordance with embodiments of the present invention, in accordance with embodiments of the present invention.

FIG. 3 illustrates an exemplary knowledge-based planning system 300, in accordance with embodiments of the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 170, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, e.g., comprising a previously determined predictive dynamics database that includes information regarding one or more metrics for corresponding regions of interest for a population of patients, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose and/or dose rate) can be included in the treatment planning process. The medical image processing module 316 provides automatic contouring and automatic segmentation of two-dimensional cross-sectional slides (e.g., from any imaging modality such as, but not limited to, computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 170.

In accordance with embodiments of the present invention, the optimizer model 170 may use a dose prediction model to provide model outputs. Model outputs may include, for example, a 3D dose distribution, fluences, dose rates, and/or associated dose-volume histograms (DVHs) and dose rate-dose-volume histograms (DRDVHs). These model outputs may represent a portion or all of a potential treatment plan. This information may reside in data structures in computer readable memory, e.g., stored within memories 215 and/or 220 (FIG. 2), and may be displayed, e.g., via display 225 (FIG. 2), for review by a clinician.

Due to a variety of factors, it is difficult to develop a treatment plan that meets the criteria to achieve benefits of FLASH radiotherapy, both within a target volume and in adjacent structures, including, for example, organs at risk (OARs). Such difficulties arise, for example, due to technology limitations of a radiotherapy system, e.g., limitations of dose rate, limitations of beam diameter, and/or limitations of beam aim.

Conventional displays of a potential radiation therapy treatment plan are not satisfactory in indicating dose rates of radiation that are to be delivered to a patient. For example, conventional displays of a potential radiation therapy treatment plan do not satisfactorily indicate what portions of such a treatment plan correspond to FLASH radiotherapy, e.g., achieve a "FLASH effect." In accordance with embodiments of the present invention, a graphical user interface control device or element may determine a dose rate and/or a range of dose rates of a radiation therapy treatment plan display.

Figure 4A:
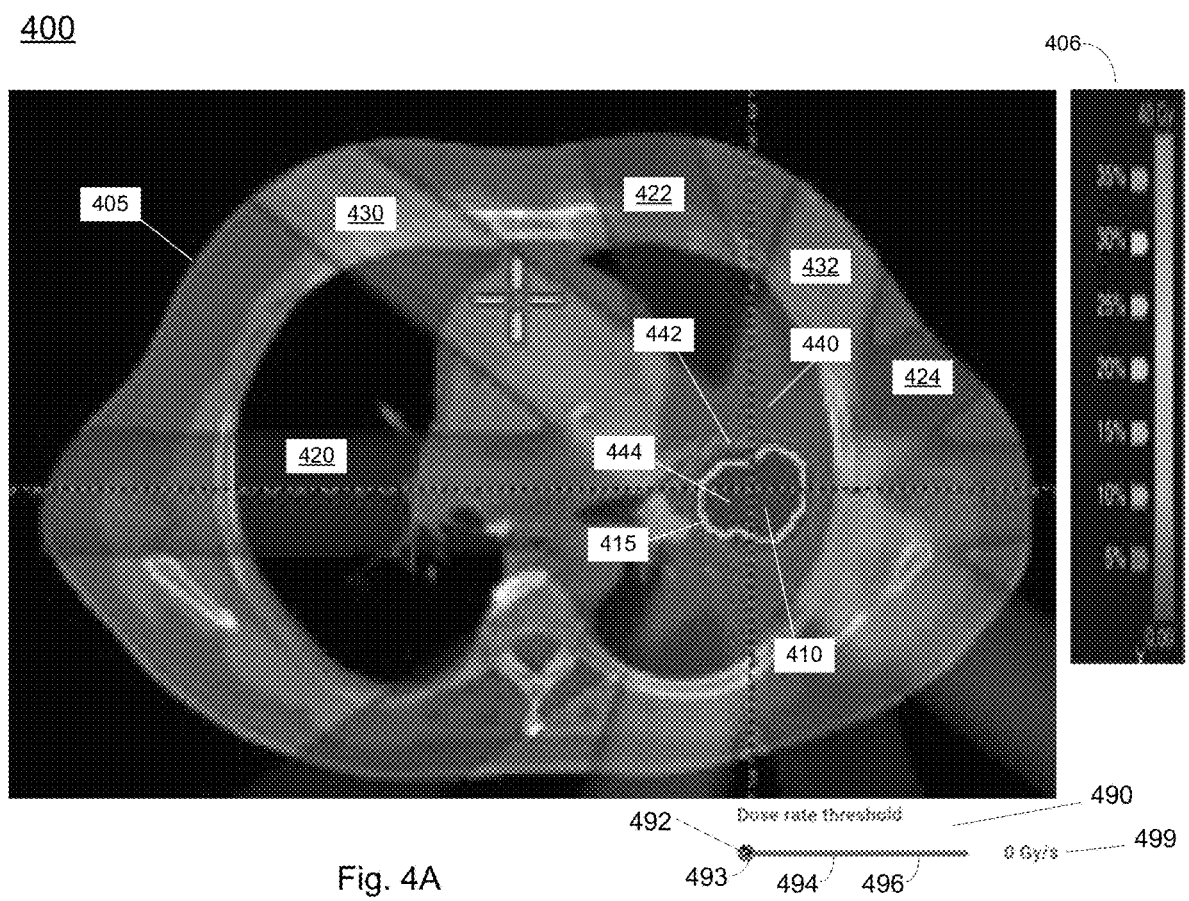
FIG. 4A illustrates an exemplary axial cross section display image of a simulated patient treatment plan based on first setting of a dose rate slider, in accordance with embodiments of the present invention.

FIG. 4A illustrates an exemplary axial cross section display image 400 of a simulated patient treatment plan, in accordance with embodiments of the present invention. An axial cross section image is one of several anatomical planes well know and used in the radiotherapy arts.

Embodiments in accordance with the present invention are well suited to the use of sagittal and/or coronal plane displays instead of and/or in addition, as well. Display image 400 may be displayed on display unit 125 of FIG. 1 in some embodiments. In the example of FIG. 4A, display image 400 may generally correspond to a radiation therapy treatment plan for a lung tumor 410. In general, the color intensity within display image 400 identifies a total radiation dose for the areas indicated. Legend 406 illustrates an exemplary color coding dose legend for display image 400. For example, black areas receive little or no radiation. Blue indicates a relatively lower dose, green indicates a relatively higher dose in comparison to the dose indicated by blue, while red indicates a relatively higher still dose. Other color codings may be used in embodiments, and are considered within the scope of the present invention.

Blue-green outline 415 identifies an outline of the tumor 410. The grey outline 405 indicates a patient's skin, fat, and surface muscles. Radiation fields 420, 422, 424 are shaded blue, indicating these fields receive a relatively lower dose of radiation. Radiation fields 430, 432 are in a "lighter" blue-green color, indicating a relatively higher radiation dose in comparison to fields 420, 422, 424. Fields near the tumor are colored so as to indicate higher doses of radiation. For example, field 440 is colored green, indicating a relatively higher radiation dose in comparison to fields 430, 432. Field 442 is presented in a yellow color, indicating a relatively higher radiation dose in comparison to field 440. Field 444 is presented in a red color, indicating the highest radiation dose of the treatment plan. Under the conventional art, the colors correspond to a total radiation dose, and do not reflect a dose rate.

Figure 4B:
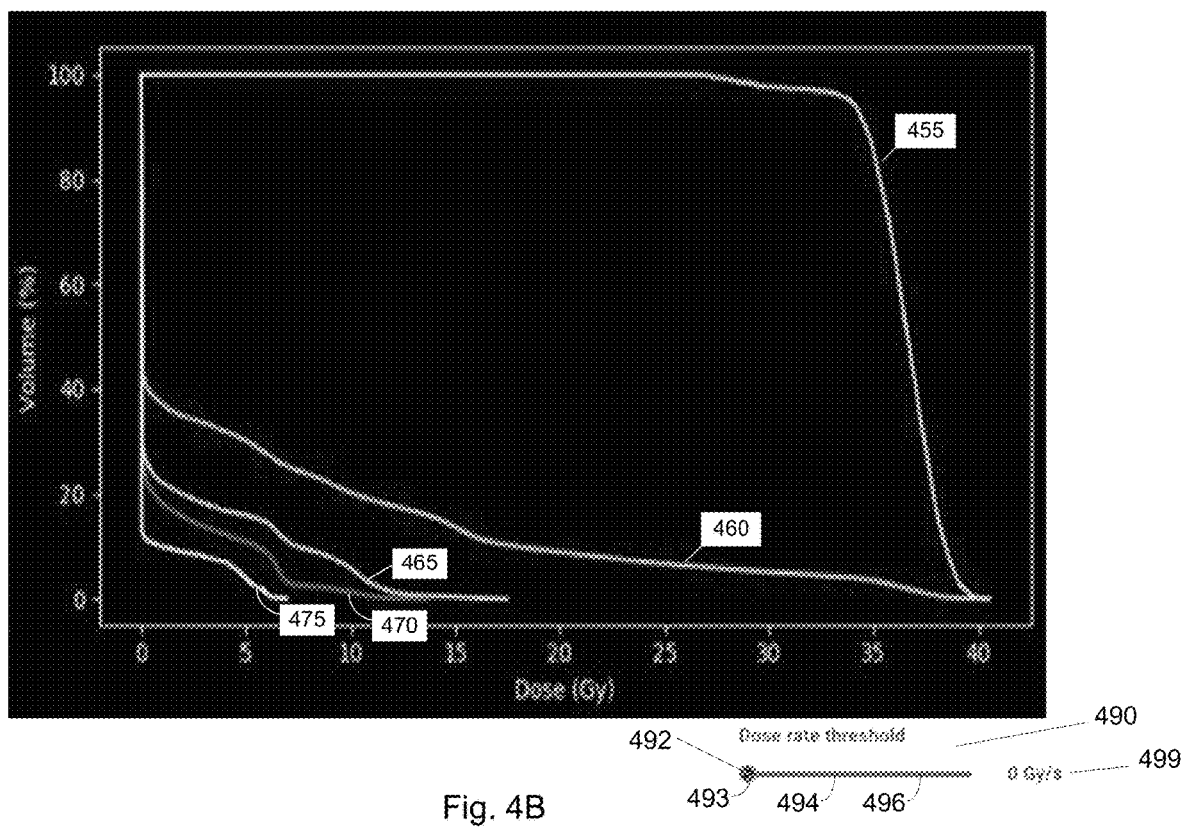
FIG. 4B illustrates an exemplary dose-volume histogram of a simulated patient treatment plan based on first setting of a dose rate slider, in accordance with embodiments of the present invention.

FIG. 4B illustrates an exemplary dose-volume histogram (DVH) 450 of a simulated patient treatment plan, in accordance with embodiments of the present invention. DVH display 450 is for the same radiation treatment plan as axial cross section display image 400 of FIG. 4A. DVH display 450 may be displayed in association with display image 400

(FIG. 4A), e.g., above, below, or to a side of display image 400, in some embodiments. Dose-volume histogram image 450 comprises a series of plots or curves 455, 460, 465, 470, 475 corresponding to total radiation doses delivered to various patient regions, tissues, and/or organs at risk (OARs) for the simulated patient treatment plan. For example, curve 455, presented in a teal color, may correspond to a planning target volume (PTV) for the tumor 410, which is a well known type of radiation treatment volume. Curve 460, presented in a lime green color, may correspond to a tracheobronchial region of the patient. Curve 465, presented in a magenta color, may correspond to a heart region of the patient. Curve 470, presented in a dark green color, may correspond to an esophageal region of the patient. Curve 475, presented in a yellow color, may correspond to a spinal cord region of the patient. Dose-volume histogram image 450 is well suited to display other curves corresponding to other patient regions, tissues, and/or organs at risk (OARs) for the simulated patient treatment plan, including, for example, Lungs-gross tumor volume (GTV), and/or Great Vessels. Under the conventional art, the curves 455, 460, 465, 470, 475 correspond to a total radiation dose for a particular region, tissue type, and/or OAR, and do not reflect a dose rate. It is appreciated that the colors used in display image 450 may not necessarily correspond to the colors used in display image 400 (FIG. 4A).

In accordance with embodiments of the present invention, a graphical user interface (GUI) control device or element 490 is provided on the GUI of display image 400 (FIG. 4A) and/or display image 450 (FIG. 4B). GUI control device 490 is known as or referred to as a "dose rate slider." Dose rate slider 490 indicates and allows a user to select a range of dose rates to be displayed in presentations of a radiation treatment plan, for example, in display images 400 and/or 450. Dose rate slider may be presented horizontally, as show in the embodiment of FIG. 4A, or it may be presented vertically, in embodiments.

Dose rate slider 490 comprises elements common to slider graphical user interfaces, for example a "thumb" 492 (also known as a "handle" or "knob") and a "track" 494. As the slider's 490 value changes, a portion of the track 494 between the thumb 492 value and an end of track 494 may fill with color highlight 496, in some embodiments. Thumb 492 may comprise a direction arrow 493, in some embodiments, although that is not required. Direction arrow 493 indicates to a user which portion of track 494, e.g., to the right or to the left of thumb 492, is selecting a range of dose rates.

A position of thumb 492 may be changed by a user. For example, thumb 492 may be "grabbed" and "dragged" by a user operating a mouse and/or a trackball device. Thumb 492 may be moved responsive to user touch, e.g., on a touch-sensitive display. Thumb 492 may be moved responsive to a keyboard input, e.g., via "arrow" or "+" or "–" key(s). Thumb 492 may be moved responsive direct numeric input, e.g., via a keyboard or number pad. Thumb 492 may be moved responsive to a rotary encoding device, including, for example, a thumbwheel or a dial. Thumb 492 may be moved responsive to voice command(s). Thumb 492 may be moved responsive to user gestures.

In the embodiments of FIGS. 4A and 4B, dose rate slider 490 is set to, and indicates that exemplary axial cross section display image 400 (FIG. 4A) and dose-volume histogram 450 (FIG. 4B) show information of all dose rates greater than 0, e.g., all dose rates. For example, the thumb 492 of dose rate slider 490 is positioned at the left extend of the slider's track 494, and the dose rate slider 490 track is filled 496 or highlighted to the right of the thumb 492. The text 499 confirms that the dose rate threshold is set to 0 Gy/s. It is appreciated that, as illustrated, with a dose rate threshold set to 0 Gy/s, exemplary axial cross section display image 400 (FIG. 4A) and dose-volume histogram 450 (FIG. 4B) are equivalent to the conventional art. For example, exemplary axial cross section display image 400 displays total dose information for the radiation fields, and dose-volume histogram 450 displays total dose information for the indicated regions, tissues, and/or organs at risk.

Figure 5A:
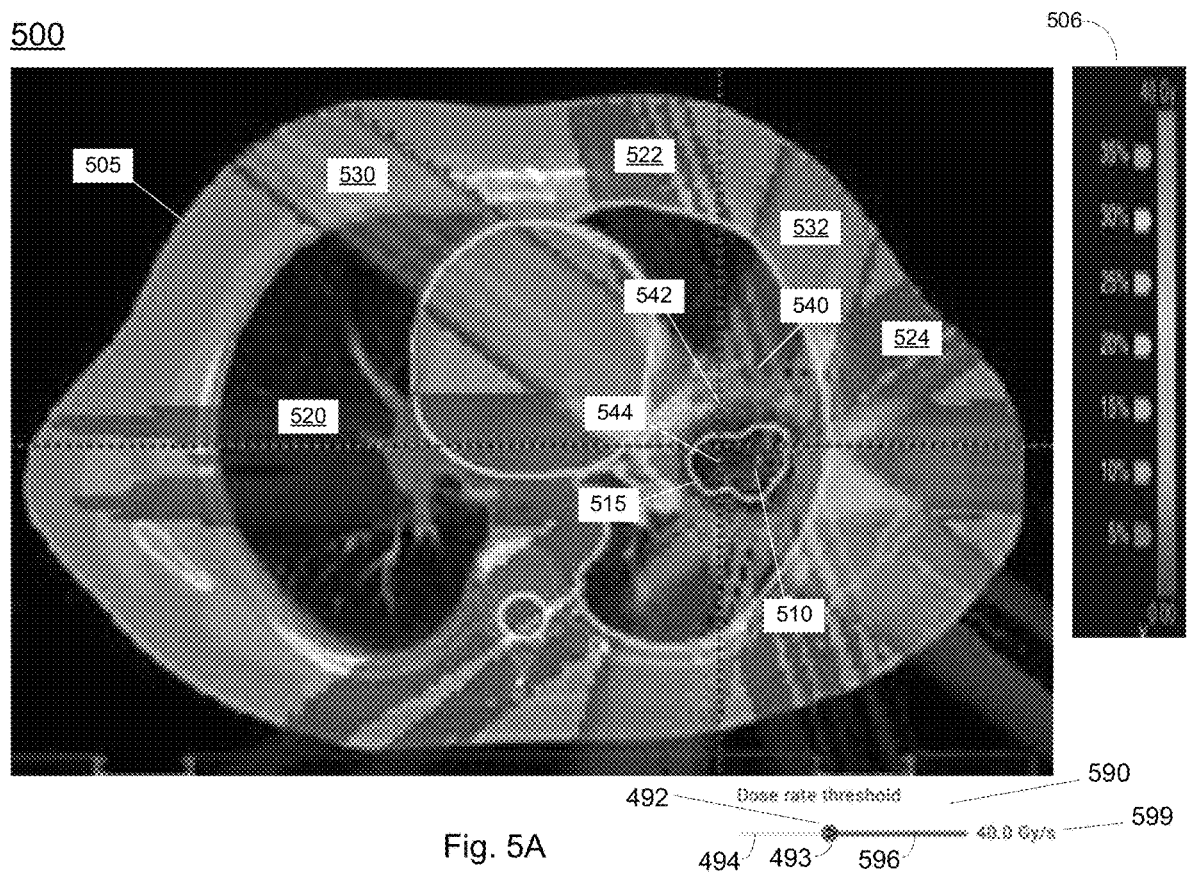
FIG. 5A illustrates an exemplary axial cross section display image of a simulated patient treatment plan based on second setting of a dose rate slider, in accordance with embodiments of the present invention.

FIG. 5A illustrates an exemplary axial cross section display image 500 of a simulated patient treatment plan, in accordance with embodiments of the present invention. Embodiments in accordance with the present invention are well suited to the use of sagittal and/or coronal plane displays instead of and/or in addition, as well. Image 500 may be displayed on display unit 125 of FIG. 1 in some embodiments. In the example of FIG. 5A, display image 500 may generally correspond to a radiation therapy treatment plan for a lung tumor 510.

In the embodiment of FIG. 5A, dose rate slider 590 is set to, and indicates that axial cross section display image 500 displays information of radiation doses that are delivered at a rate of 40.0 Gy/s or greater, in contrast to the conventional art display of a total dose, independent of dose rate. Text 599 displays this value. Color highlight 596 indicates that the dose rate range is above or to the right of the thumb 492 value.

In general, the color intensity within display image 500 identifies a radiation dose delivered at a rate of 40.0 Gy/s or greater for the areas indicated. Legend 506 illustrates an exemplary color coding dose legend for display image 500. For example, black areas receive little or no radiation. Blue indicates a relatively lower dose, green indicates a relatively higher dose in comparison to the dose indicated by blue, while red indicates a relatively higher still dose. Other color codings may be used in embodiments, and are considered within the scope of the present invention.

Blue-green outline 515 identifies an outline of the tumor 510. The grey outline 505 indicates a patient's skin, fat, and surface muscles. Radiation fields 520, 522, 524 are shaded blue, indicating these fields receive a relatively lower dose of radiation. Radiation fields 530, 532 are in a "lighter" blue-green color, indicating a relatively higher radiation dose in comparison to fields 520, 522, 524. Fields near the tumor are colored so as to indicate higher doses of radiation. For example, field 540 is colored green, indicating a relatively higher radiation dose in comparison to fields 530, 532. Field 542 is presented in a yellow color, indicating a relatively higher radiation dose in comparison to field 540. Field 544 is presented in a red color, indicating the highest radiation dose of the treatment plan.

In comparison to axial cross section display image 400 (FIG. 4A), axial cross section display image 500 illustrates lesser dosages for the various fields. For example, field 520 indicates a lesser dose in comparison to field 420 of FIG. 4A. This occurs because axial cross section display image 500 displays only a portion of the total radiation dose, e.g., radiation doses delivered at dose rate greater than or equal to 40 Gy/s, as indicated and/or selected by dose rate slider 590. Those dosages delivered at a rate less than 40 Gy/s are not shown in axial cross section display image 500, unlike in axial cross section display image 400 (FIG. 4A).

Figure 5B:
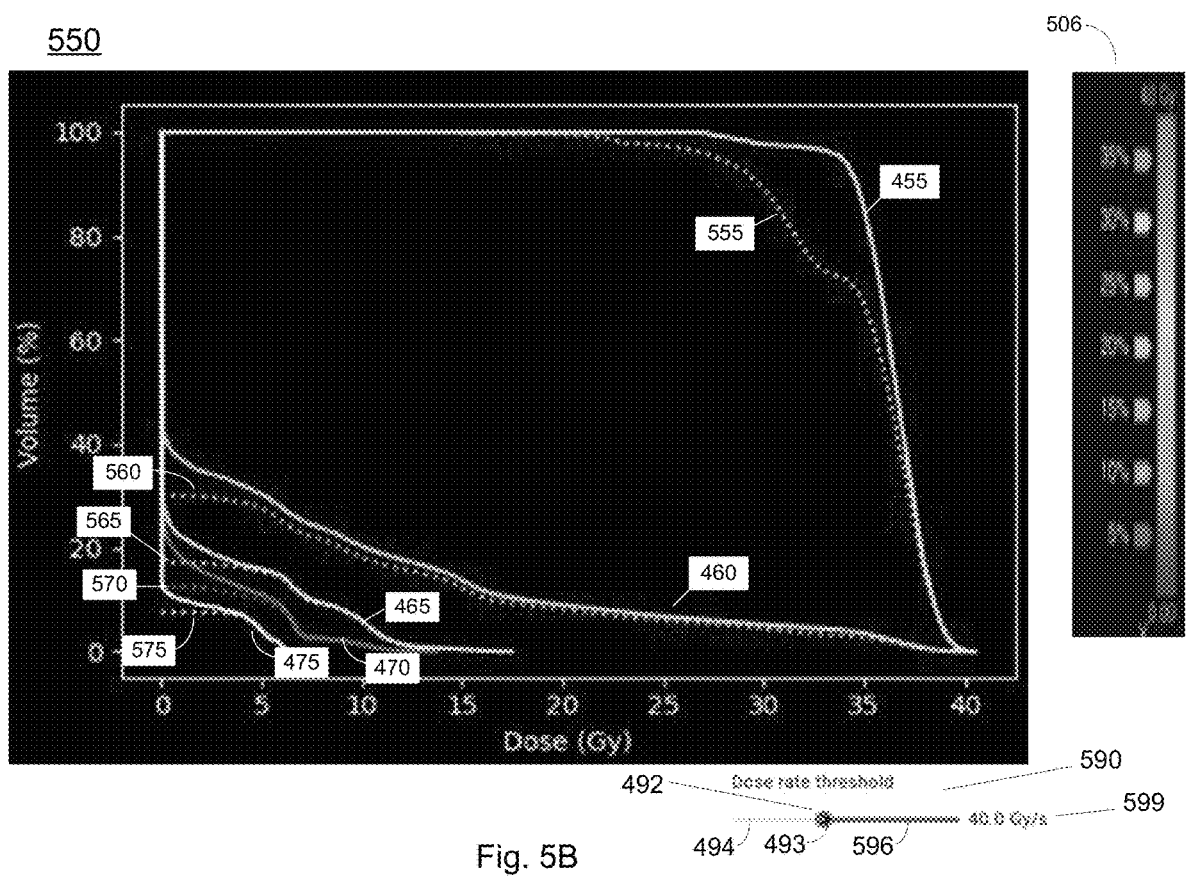
FIG. 5B illustrates an exemplary dose-volume histogram of a simulated patient treatment plan based on second setting of a dose rate slider, in accordance with embodiments of the present invention.

FIG. 5B illustrates an exemplary dose-volume histogram (DVH) 550 of a simulated patient treatment plan, in accordance with embodiments of the present invention. DVH display 550 is for the same radiation treatment plan as axial cross section display image 500 of FIG. 5A, as well as the same radiation treatment plan of FIGS. 4A and 4B. DVH display 550 may be displayed in association with display image 500 (FIG. 5A), e.g., above, below, or to a side of display image 500, in some embodiments. Dose-volume histogram image 550 comprises a series of plots or curves 455, 460, 465, 470, 475 corresponding to total radiation doses delivered to various patient regions, tissues, and/or organs at risk (OARs) for the simulated patient treatment plan, as previously presented with respect to FIG. 4B. It is appreciated that the colors used in display image 550 may not necessarily correspond to the colors used in display image 500 (FIG. 5A).

In addition to total dose curves 455, 460, 465, 470, 475, indicated by solid lines, dose-volume histogram 550 displays a series of dotted-line curves 555, 560, 565, 570, 575. The dotted line curves 555, 560, 565, 570, 575 indicate doses received by the particular region, tissue and/or organs at risk at or above a dose rate of 40 Gy/s, as indicated and/or selected by dose rate slider 590. The dotted line curves 555, 560, 565, 570, 575 may be displayed in the same colors corresponding to the total dose curves 455, 460, 465, 470, 475, in embodiments. Other methods of showing a correspondence between a curve or graph representing a total dose and a curve representing a dose delivered based on a dose rate criteria are well suited to embodiments in accordance with the present invention and are considered within the scope of the present invention. The area between two corresponding curves, e.g., solid line curve 455 and dotted line curve 555, may be visually indicated, for example, by a solid fill and/or a cross hatching pattern, in some embodiments.

For example, dotted line curve 555, presented in a teal color, may indicate a dosage delivered at or above a selected dosage rate, e.g., greater than or equal to 40 Gy/s, for a planning target volume (PTV) for the tumor 510, which is a well known type of radiation treatment volume. Dotted line curve 560, presented in a lime green color, may indicate a dosage delivered at or above a selected dosage rate, e.g., greater than or equal to 40 Gy/s, for a tracheobronchial region of the patient. Dotted line curve 565, presented in a magenta color, may indicate a dosage delivered at or above a selected dosage rate, e.g., greater than or equal to 40 Gy/s, for a heart region of the patient. Dotted line curve 570, presented in a dark green color, may indicate a dosage delivered at or above a selected dosage rate, e.g., greater than or equal to 40 Gy/s, for an esophageal region of the patient. Dotted line curve 575, presented in a yellow color, may indicate a dosage delivered at or above a selected dosage rate, e.g., greater than or equal to 40 Gy/s, for a spinal cord region of the patient. Dose-volume histogram image 550 is well suited to display other dotted line curves indicating a dosage delivered at or above a selected dosage rate, e.g., greater than or equal to 40 Gy/s, for other patient regions, tissues, and/or organs at risk (OARs) for the simulated patient treatment plan, including, for example, Lungs-gross tumor volume (GTV), and/or Great Vessels.

In accordance with embodiments of the present invention, a difference between a total dosage curve, e.g., solid line curve 455, and a corresponding dose-rate-based dotted line curve, e.g., dotted line curve 555, provides a visual indication of a difference between a total radiation dose for a particular region, tissue and/or OAR, and a dose delivered at or above a selected dosage rate, e.g., greater than or equal to 40 Gy/s. In accordance with embodiments of the present invention, a dose-rate-based dotted line curve, e.g., dotted curve 555, may indicate a portion of a radiation treatment plan that achieves a "FLASH effect."

Figure 6A:
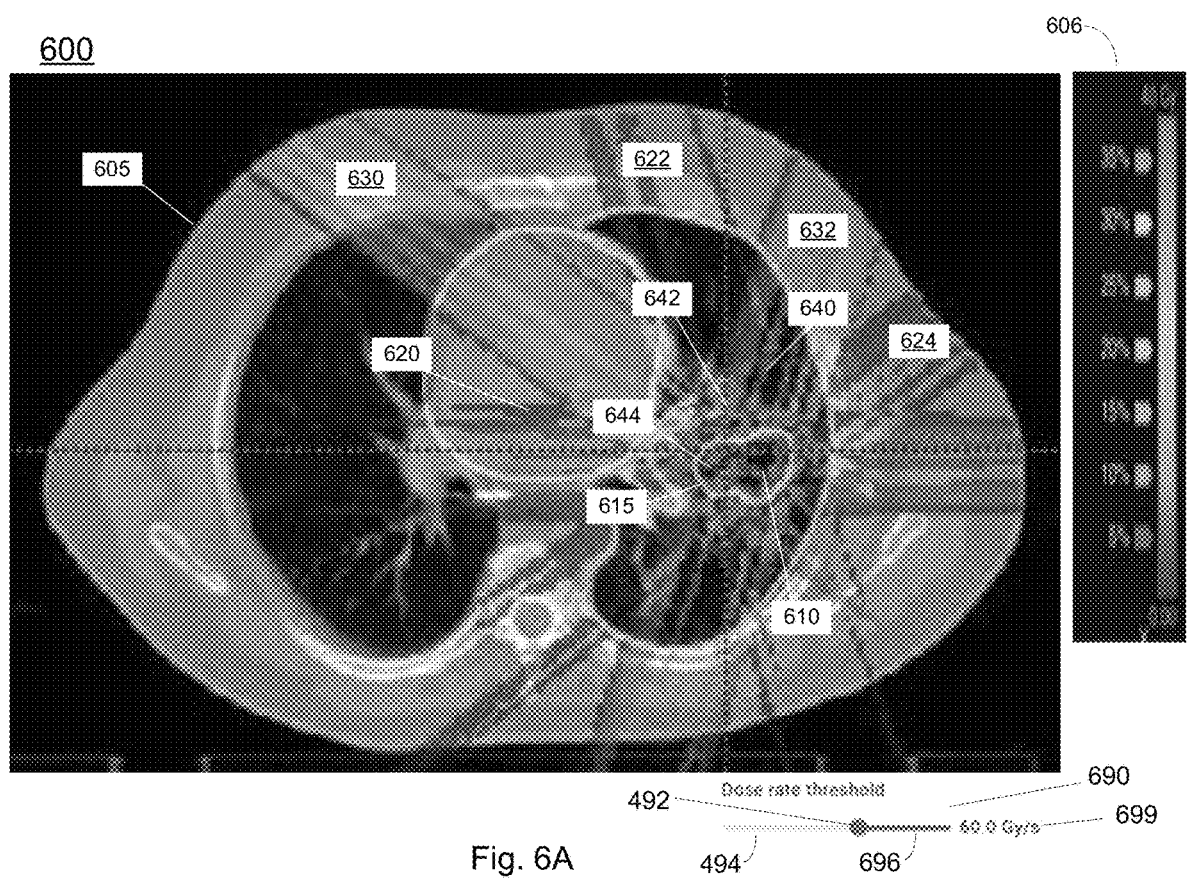
FIG. 6A illustrates an exemplary axial cross section display image of a simulated patient treatment plan based on third setting of a dose rate slider, in accordance with embodiments of the present invention.

FIG. 6A illustrates an exemplary axial cross section display image 600 of a simulated patient treatment plan, in accordance with embodiments of the present invention. Embodiments in accordance with the present invention are well suited to the use of sagittal and/or coronal plane displays instead of and/or in addition, as well. Image 600 may be displayed on display unit 125 of FIG. 1 in some embodiments. In the example of FIG. 6A, display image 600 may generally correspond to a radiation therapy treatment plan for a lung tumor 610.

In the embodiment of FIG. 6A, dose rate slider 690 is set to, and indicates that axial cross section display image 600 displays information of radiation doses that are delivered at a rate of 60.0 Gy/s or greater, in contrast to the conventional art display of a total dose, independent of dose rate. Text 699 displays this value. Color highlight 696 indicates that the dose rate range is above or to the right of the thumb 492 value.

In general, the color intensity within display image 600 identifies a radiation dose delivered at a rate of 60.0 Gy/s or greater for the areas indicated. Legend 606 illustrates an exemplary color coding dose legend for display image 600. For example, black areas receive little or no radiation. Blue indicates a relatively lower dose, green indicates a relatively higher dose in comparison to the dose indicated by blue, while red indicates a relatively higher still dose. Other color codings may be used in embodiments, and are considered within the scope of the present invention.

Blue-green outline 615 identifies an outline of the tumor 610. The grey outline 605 indicates a patient's skin, fat, and surface muscles. Radiation fields 620, 622, 624 are shaded blue, indicating these fields receive a relatively lower dose of radiation. Radiation fields 630, 632 are in a "lighter" blue-green color, indicating a relatively higher radiation dose in comparison to fields 620, 622, 624. Fields near the tumor are colored so as to indicate higher doses of radiation. For example, field 640 is colored green, indicating a relatively higher radiation dose in comparison to fields 630, 632. Field 642 is presented in a yellow color, indicating a relatively higher radiation dose in comparison to field 640. Field 644 is presented in a red color, indicating the highest radiation dose of the treatment plan.

In comparison to axial cross section display image 400 (FIG. 4A) and/or axial cross section display image 500 (FIG. 5A), axial cross section display image 600 illustrates lesser dosages for the several fields. For example, field 620 indicates a lesser dose in comparison to field 420 of FIG. 4A and in comparison to field 520 of FIG. 5A. Further, there is much less red color present in display image 600, indicating a high radiation dose, in displays image 600 in comparison to display image 400 (FIG. 4A). This occurs because axial cross section display image 600 displays only a portion of the total radiation dose, e.g., radiation doses delivered at dose rate greater than or equal to 60 Gy/s, as indicated and/or selected by dose rate slider 690. Those dosages delivered at a rate less than 60 Gy/s are not shown in axial cross section display image 600, unlike in axial cross section display image 400 (FIG. 4A).

Figure 6B:
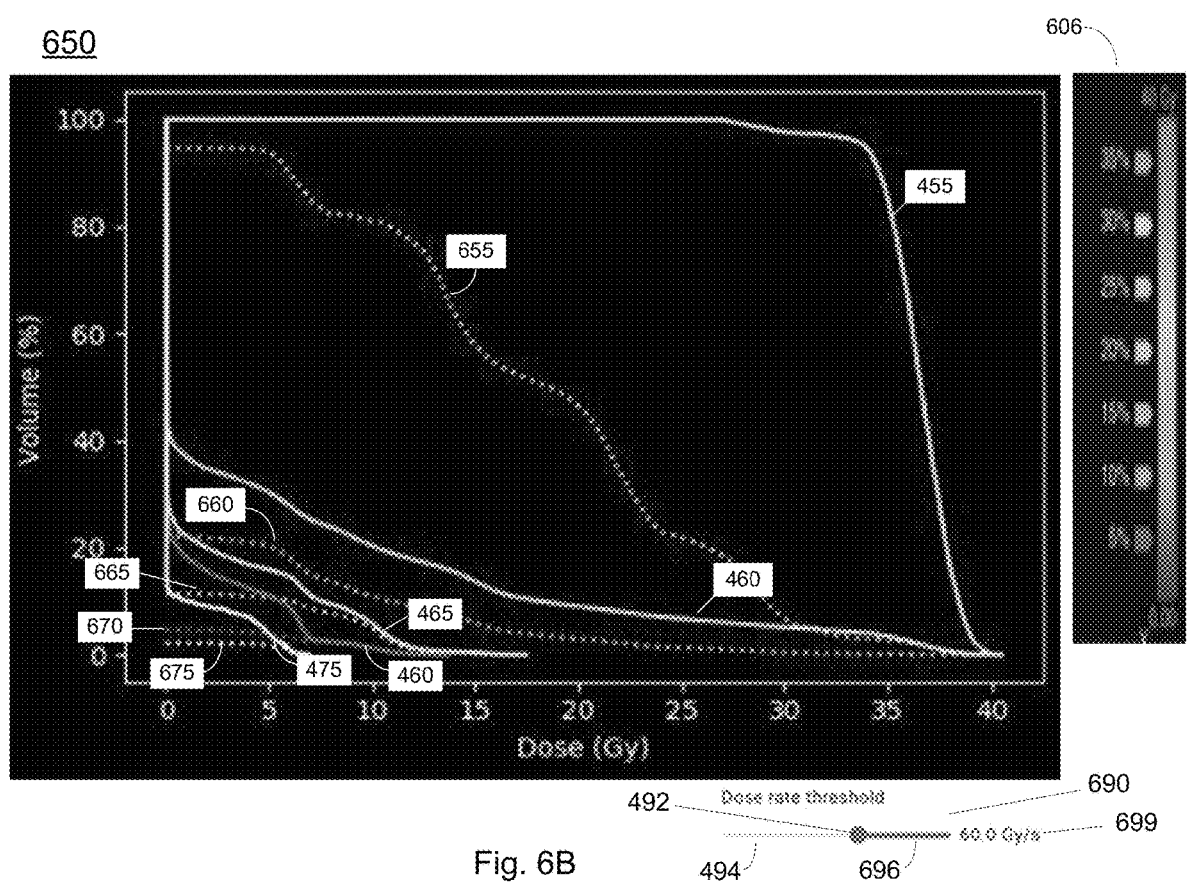
FIG. 6B illustrates an exemplary dose-volume histogram of a simulated patient treatment plan based on third setting of a dose rate slider, in accordance with embodiments of the present invention.

FIG. 6B illustrates an exemplary dose-volume histogram (DVH) 650 of a simulated patient treatment plan, in accordance with embodiments of the present invention. DVH display 650 is for the same radiation treatment plan as axial cross section display image 600 of FIG. 6A, as well as the same radiation treatment plan of FIGS. 4A, 4B, 5A and 5B. DVH display 650 may be displayed in association with display image 600 (FIG. 6A), e.g., above, below, or to a side of display image 600, in some embodiments. Dose-volume histogram image 650 comprises a series of plots or curves 455, 460, 465, 470, 475 corresponding to total radiation doses delivered to various patient regions, tissues, and/or organs at risk (OARs) for the simulated patient treatment plan, as previously presented with respect to FIG. 4B. It is appreciated that the colors used in display image 650 may not necessarily correspond to the colors used in display image 600 (FIG. 6A).

In addition to total dose curves 455, 460, 465, 470, 475, indicated by solid lines, dose-volume histogram 650 displays a series of dotted-line curves 655, 660, 665, 670, 675. The dotted line curves 655, 660, 665, 670, 675 indicate doses received by the particular region, tissue and/or organs at risk at or above a dose rate of 60 Gy/s, as indicated and/or selected by dose rate slider 690. The dotted line curves 655, 660, 665, 670, 675 may be displayed in the same colors corresponding to the total dose curves 455, 460, 465, 470, 475, in embodiments. Other methods of showing a correspondence between a curve or graph representing a total dose and a curve representing a dose delivered based on a dose rate criteria are well suited to embodiments in accordance with the present invention and are considered within the scope of the present invention. The area between two corresponding curves, e.g., solid line curve 455 and dotted line curve 655, may be visually indicated, for example, by a solid fill and/or a cross hatching pattern, in some embodiments.

For example, dotted line curve 655, presented in a teal color, may indicate a dosage delivered at or above a selected dosage rate, e.g., greater than or equal to 60 Gy/s, for a planning target volume (PTV) for the tumor 610, which is a well known type of radiation treatment volume. Dotted line curve 660, presented in a lime green color, may indicate a dosage delivered at or above a selected dosage rate, e.g., greater than or equal to 60 Gy/s, for a tracheobronchial region of the patient. Dotted line curve 665, presented in a magenta color, may indicate a dosage delivered at or above a selected dosage rate, e.g., greater than or equal to 60 Gy/s, for a heart region of the patient. Dotted line curve 670, presented in a dark green color, may indicate a dosage delivered at or above a selected dosage rate, e.g., greater than or equal to 60 Gy/s, for an esophageal region of the patient. Dotted line curve 675, presented in a yellow color, may indicate a dosage delivered at or above a selected dosage rate, e.g., greater than or equal to 60 Gy/s, for a spinal cord region of the patient. Dose-volume histogram image 650 is well suited to display other dotted line curves indicating a dosage delivered at or above a selected dosage rate, e.g., greater than or equal to 60 Gy/s, for other patient regions, tissues, and/or organs at risk (OARs) for the simulated patient treatment plan, including, for example, Lungs-gross tumor volume (GTV), and/or Great Vessels.

In accordance with embodiments of the present invention, a difference between a total dosage curve, e.g., solid line curve 455, and a corresponding dose-rate-based dotted line curve, e.g., dotted line curve 655, provides a visual indication of a difference between a total radiation dose for a particular region, tissue and/or OAR, and a dose delivered at or above a selected dosage rate, e.g., greater than or equal to 60 Gy/s.

Figure 7A:
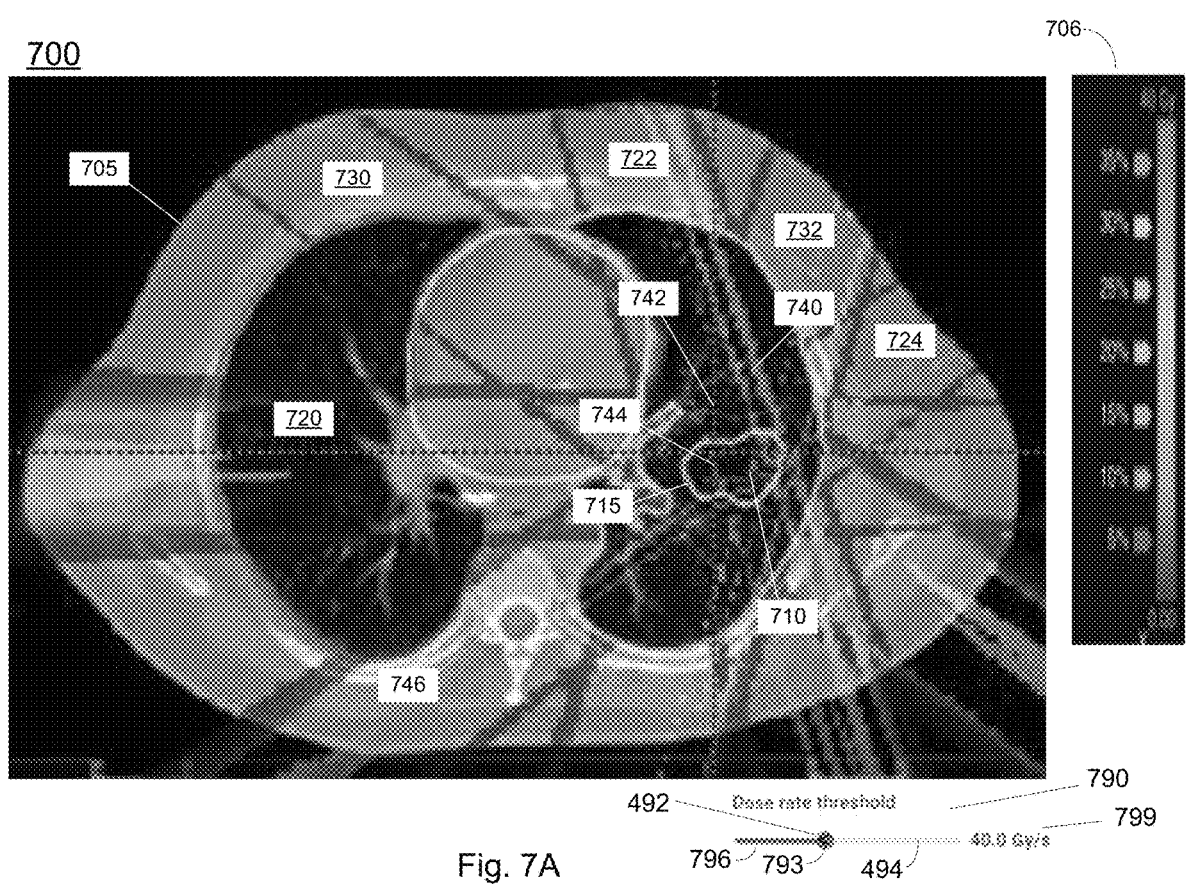
FIG. 7A illustrates an exemplary axial cross section display image of a simulated patient treatment plan based on fourth setting of a dose rate slider, in accordance with embodiments of the present invention.

FIG. 7A illustrates an exemplary axial cross section display image 700 of a simulated patient treatment plan, in accordance with embodiments of the present invention. Embodiments in accordance with the present invention are well suited to the use of sagittal and/or coronal plane displays instead of and/or in addition, as well. Image 700 may be displayed on display unit 125 of FIG. 1 in some embodiments. In the example of FIG. 7A, display image 700 may generally correspond to a radiation therapy treatment plan for a lung tumor 710.

In the embodiment of FIG. 7A, dose rate slider 790 is set to, and indicates that axial cross section display image 600 displays information of radiation doses that are delivered at a rate of 40.0 Gy/s or less, in contrast to the conventional art display of a total dose, independent of dose rate. Text 799 displays this value. Color highlight 796 indicates that the dose rate range is below or to the left of the thumb 492 value. Optional arrow 793 also indicates that the selected range of dose rates is to the left of the thumb 492.

In general, the color intensity within display image 700 identifies a radiation dose delivered at a rate of 40.0 Gy/s or less for the areas indicated. Legend 706 illustrates an exemplary color coding dose legend for display image 700. For example, black areas receive little or no radiation. Blue indicates a relatively lower dose, green indicates a relatively higher dose in comparison to the dose indicated by blue, while red indicates a relatively higher still dose. Other color codings may be used in embodiments, and are considered within the scope of the present invention.

Blue-green outline 715 identifies an outline of the tumor 710. The grey outline 705 indicates a patient's skin, fat, and surface muscles. Radiation fields 720, 722, 724 are shaded blue, indicating these fields receive a relatively lower dose of radiation. Radiation fields 730, 732 are in a "lighter" blue-green color, indicating a relatively higher radiation dose in comparison to fields 720, 722, 724. Fields near the tumor are colored so as to indicate lesser doses of radiation for the selected range of dose rates. For example, field 740 is colored green, indicating a relatively higher radiation dose in comparison to fields 730, 732. Field 742 is presented in blue and black colors, indicating a relatively lower dose. Field 744 comprises little color, indicating that this area receives little radiation at or below the selected dose rate, e.g., less than or equal to 40 Gy/s. This may be desirable for a radiation therapy treatment plan. For example, a clinician may want most or all of the radiation delivered to tumor 710 to be at high dose rates.

Area 746 is indicated in a yellow color. This indicates that region 746 receives a relatively high radiation dose at low dose rates, e.g., at a rate less than or equal to 40 Gy/s. This may be desirable for a radiation therapy treatment plan. For example, a clinician may want most or all of the radiation delivered to area 476 to be at low dose rates.

In comparison to axial cross section display image 400 (FIG. 4A) and/or axial cross section display image 500 (FIG. 5A), axial cross section display image 700 illustrates lesser dosages for the several fields. For example, field 720 indicates a lesser dose in comparison to field 420 of FIG. 4A and in comparison to field 520 of FIG. 5A. Further, there is much less red color present in display image 700, indicating a high radiation dose, in displays image 700 in comparison to display image 400 (FIG. 4A). This occurs because axial cross section display image 700 displays only a portion of the total radiation dose, e.g., radiation doses delivered at dose rate less than or equal to 40 Gy/s, as indicated and/or selected by dose rate slider 790. Those dosages delivered at a rate greater than 40 Gy/s are not shown in axial cross section display image 700, unlike in axial cross section display image 400 (FIG. 4A).

Figure 7B:
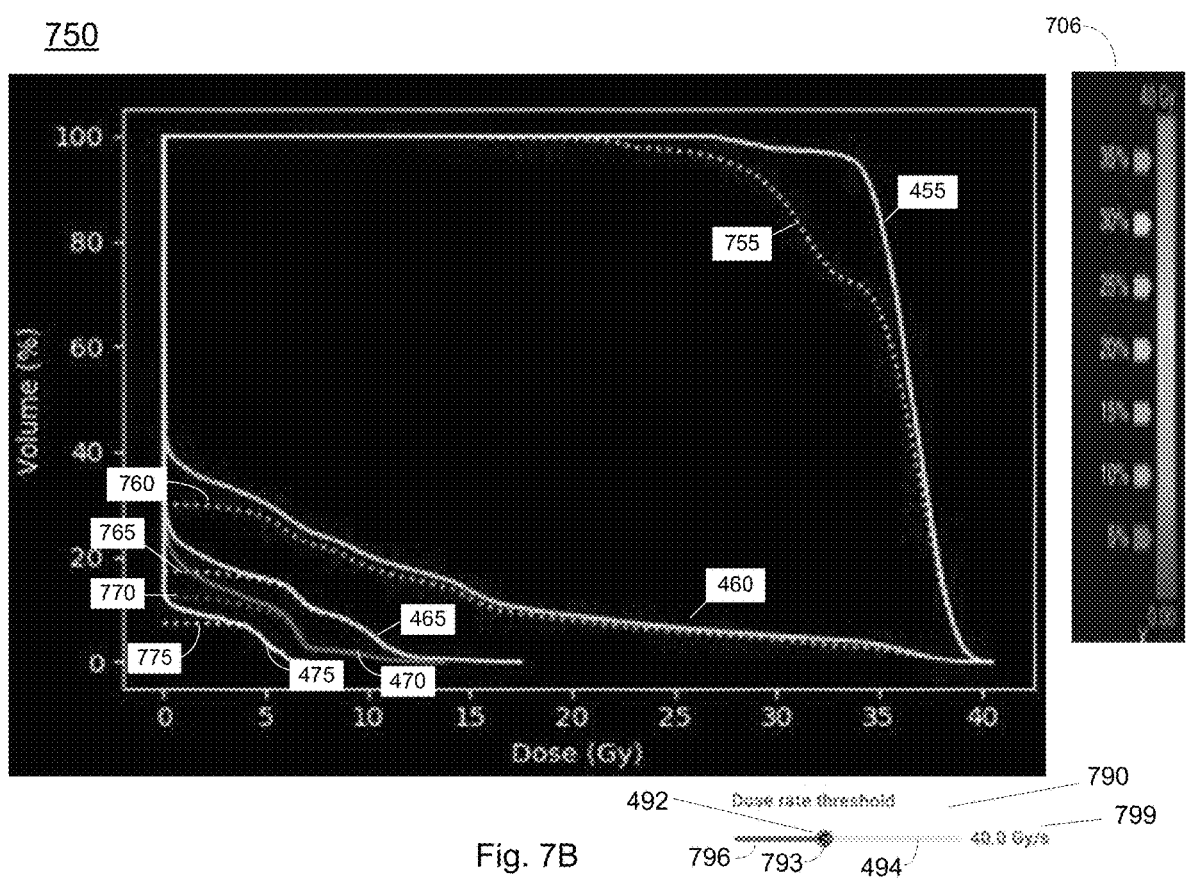
FIG. 7B illustrates an exemplary dose-volume histogram of a simulated patient treatment plan based on fourth setting of a dose rate slider, in accordance with embodiments of the present invention.

FIG. 7B illustrates an exemplary dose-volume histogram (DVH) 750 of a simulated patient treatment plan, in accordance with embodiments of the present invention. DVH display 750 is for the same radiation treatment plan as axial cross section display image 700 of FIG. 7A, as well as the same radiation treatment plan of FIGS. 4A, 4B, 5A, 5B, 6A, and 6B. DVH display 750 may be displayed in association with display image 700 (FIG. 7A), e.g., above, below, or to a side of display image 700, in some embodiments. Dose-volume histogram image 750 comprises a series of plots or curves 455, 460, 465, 470, 475 corresponding to total radiation doses delivered to various patient regions, tissues, and/or organs at risk (OARs) for the simulated patient treatment plan, as previously presented with respect to FIG. 4B. It is appreciated that the colors used in display image 750 may not necessarily correspond to the colors used in display image 700 (FIG. 7A).

In addition to total dose curves 455, 460, 465, 470, 475, indicated by solid lines, dose-volume histogram 750 displays a series of dotted-line curves 755, 760, 765, 770, 775. The dotted line curves 755, 760, 765, 770, 775 indicate doses received by the particular region, tissue and/or organs at risk at or below a dose rate of 40 Gy/s, as indicated and/or selected by dose rate slider 790. The dotted line curves 755, 760, 765, 770, 775 may be displayed in the same colors corresponding to the total dose curves 455, 460, 465, 470, 475, in embodiments. Other methods of showing a correspondence between a curve or graph representing a total dose and a curve representing a dose delivered based on a dose rate criteria are well suited to embodiments in accordance with the present invention and are considered within the scope of the present invention. The area between two corresponding curves, e.g., solid line curve 455 and dotted line curve 755, may be visually indicated, for example, by a solid fill and/or a cross hatching pattern, in some embodiments.

For example, dotted line curve 755, presented in a teal color, may indicate a dosage delivered at or below a selected dosage rate, e.g., less than or equal to 40 Gy/s, for a planning target volume (PTV) for the tumor 710, which is a well known type of radiation treatment volume. Dotted line curve 760, presented in a lime green color, may indicate a dosage delivered at or above a selected dosage rate, e.g., less than or equal to 40 Gy/s, for a tracheobronchial region of the patient. Dotted line curve 765, presented in a magenta color, may indicate a dosage delivered at or above a selected dosage rate, e.g., less than or equal to 40 Gy/s, for a heart region of the patient. Dotted line curve 770, presented in a dark green color, may indicate a dosage delivered at or above a selected dosage rate, e.g., greater than or equal to 60 Gy/s, for an esophageal region of the patient. Dotted line curve 775, presented in a yellow color, may indicate a dosage delivered at or above a selected dosage rate, e.g., less than or equal to 40 Gy/s, for a spinal cord region of the patient. Dose-volume histogram image 750 is well suited to display other dotted line curves indicating a dosage delivered at or above a selected dosage rate, e.g., less than or equal to 40 Gy/s, for other patient regions, tissues, and/or organs at risk (OARs) for the simulated patient treatment plan, including, for example, Lungs-gross tumor volume (GTV), and/or Great Vessels.

Generation of display images of a radiation treatment plan, e.g., display images 400 (FIG. 4A), 450 (FIG. 4B), 500 (FIG. 5A), 550 (FIG. 5B), 600 (FIG. 6A), 650 (FIG. 6B), 700 (FIG. 7A), and/or 750 (FIG. 7B) is computationally intensive. In general, a radiation therapy treatment planning system, e.g., radiation therapy treatment planning system 200 of FIG. 2, is not capable of generating a new set of display images, for example, generating display image 500 (FIG. 5A) in real time within an acceptable time duration responsive to a user changing a dose rate slider, e.g., from a position of dose rate slider 490 to a position of dose rate slider 590.

For example, human factors studies have shown that a period of 100 ms is a limit for a user to feel that a system is reacting instantaneously, meaning that no special feedback is necessary expect to display a result of the user's action. A display update time of greater than about 1 second is noticeable, and will generally cause a user to lose a feeling of operating directly on data. A display update time of more than a few seconds will generally cause user anxiety, for example, a user will wonder whether a system has become unresponsive. Many users subject to such update times will lose focus and attempt to perform other tasks while waiting.

In accordance with embodiments of the present invention, information required to present display images, such as display images 400 (FIG. 4A), 450 (FIG. 4B), 500 (FIG. 5A), 550 (FIG. 5B), 600 (FIG. 6A), 650 (FIG. 6B), 700 (FIG. 7A), and/or 750 (FIG. 7B), may be generated prior to presentation of such images. For example, information for all possible settings of a dose rate slider and/or information for a subset of possible settings may be generated prior to access of such information by an operator. In this manner, display images may beneficially be changed and/or updated as an operator changes a setting of a dose rate slider. For example, display images may be changed and/or updated in less than 1 second, or in 100 ms or less.

FIG. 8 is a flow chart of an exemplary computer-implemented method 800 for dynamically updating displays of radiotherapy plan information in a graphical user interface (GUI). Method 800 may operate as part of radiation therapy treatment planning system 200 (FIG. 2) executing on electronic (computer) system 100 (FIG. 1), for example. In 810, a first window, e.g., axial cross section display image 400 of FIG. 4A, comprising graphical information of the radiotherapy plan in a first format within the GUI on a computer display is displayed. In 820, a second window comprising a dose rate slider, e.g., dose rate slider 490, configured to display a range of dose rates within the GUI is displayed. In 830, user input via the dose rate slider to select the range of dose rates is accepted. For example, the dose rate slider may be changed from the configuration of dose rate slider 490 to that of dose rate slider 590 (FIG. 5A). In 840, the first window to display radiation dosage delivered at the range of dose rates is automatically updated. For example, the first window displays axial cross section display image 500 (FIG. 5A). In optional 850, updates to the first window corresponding to a plurality of dose rate ranges are precomputed, for example, to allow for faster updates of the first window.

In this manner, the novel dose rate slider enables a clinician or other operator to investigate various aspects of a radiation treatment plan that are unavailable under the conventional art. For example, embodiments in accordance with the present invention may display radiation dosages received by fields or patient areas at a range of dose rates. Embodiments also enable displays of radiation dosages above and/or below a selected dose rate. Embodiments further enable displays of radiation dosages above and/or below a selected dose rate by patient region, tissue, and/or organ(s) at risk.

Embodiments in accordance with the present invention provide systems and methods for graphical user interface control devices for radiation therapy treatment planning. In addition, embodiments in accordance with the present invention provide systems and methods for graphical user interface control devices for radiation therapy treatment planning that display dosage information based on a user selected dose rate. Further, embodiments in accordance with the present invention provide systems and methods for graphical user interface control devices for radiation therapy treatment planning that are compatible and complementary with existing systems and methods of planning and/or administering radiotherapy.

Although the invention has been shown and described with respect to a certain exemplary embodiment or embodiments, equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

Various embodiments of the invention are thus described. While the present invention has been described in particular embodiments, it should be appreciated that the invention should not be construed as limited by such embodiments, but rather construed according to the below claims.

We claim:

1. A graphical user interface configured for display on a computer display, the graphical user interface comprising: a dose rate slider configured to enable a user to directly select a range of radiation dose rates of a radiotherapy plan; and a display image configured to present an image of radiation dosage of said radiotherapy plan, the display image displaying information of radiation doses corresponding to dose rates that are greater than or equal to a lowest dose rate of said range of radiation dose rates.

2. The graphical user interface of claim 1, wherein said range is selectable among less than a first value of said dose rate slider, and more than a second value of said dose rate slider.

3. The graphical user interface of claim 1, wherein the graphical user interface is configured to display said display image in response to a user change of said dose rate slider in less than 1 second.

4. The graphical user interface of claim 3, wherein the graphical user interface is configured to display said display image responsive to a user change of said dose rate slider in 100 milliseconds (ms) or less.

5. The graphical user interface of claim 1, wherein said display image comprises a dose volume histogram, and wherein said dose volume histogram displays information of radiation doses delivered at a dose rate corresponding to said range.

6. The graphical user interface of claim 1, wherein said display image comprises an anatomical plane image, and wherein said anatomical plane image displays information of radiation doses delivered at a dose rate corresponding to said range.

7. The graphical user interface of claim 1, wherein said display image is configured to display a portion of said radiotherapy plan that corresponds to FLASH radiotherapy.

8. A computer-implemented method for dynamically updating displays of radiotherapy plan information in a graphical user interface (GUI), the computer-implemented method comprising: displaying a first window comprising graphical information of said radiotherapy plan information in a first format within the GUI on a computer display; displaying a second window comprising a dose rate slider configured to display a range of dose rates within the GUI; accepting user input via said dose rate slider to directly select said range of dose rates; and automatically updating said first window to display radiation dosage delivered at greater than or equal to a lowest dose rate of said range of dose rates.

9. The computer-implemented method of claim 8, wherein said first window comprises an anatomical plane image.

10. The computer-implemented method of claim 9, wherein said anatomical plane image comprises an axial plane image.

11. The computer-implemented method of claim 8, wherein said first window comprises a dose volume histogram.

12. The computer-implemented method of claim 8, wherein said dose rate slider is operable to select a range of dose rates from among less than a first value of said dose rate slider, and more than a second value of said dose rate slider.

13. The computer-implemented method of claim 8, wherein said updating is performed within a duration of 100 milliseconds (ms) or less.

14. The computer-implemented method of claim 8, the computer-implemented method further comprising:
    precomputing updates to said first window corresponding to a plurality of dose rate ranges.

15. The computer-implemented method of claim 8 wherein, subsequent to said updating, said first window is configured to display a portion of said radiotherapy plan information that corresponds to FLASH radiotherapy.

16. A non-transitory computer-readable storage medium having computer-executable instructions that, when executed by one or more processors, are configured to cause a computer system to perform a method for dynamically updating displays of radiotherapy plan information in a graphical user interface (GUI), the method comprising: displaying a first window comprising graphical information of said radiotherapy plan information in a first format within the GUI on a computer display; displaying a second window comprising a dose rate slider configured to display a range of dose rates within the GUI; accepting user input via said dose rate slider to directly change said range of dose rates; and automatically updating said first window to display radiation dosage delivered at greater than or equal to a lowest dose rate of said range of dose rates.

17. The non-transitory computer-readable storage medium of claim 16, wherein said first window comprises an axial plane image.

18. The non-transitory computer-readable storage medium of claim 16, wherein said first window comprises a dose volume histogram.

19. The non-transitory computer-readable storage medium of claim 16 wherein said dose rate slider is operable to select a range of dose rates from among less than a first value of said dose rate slider, and more than a second value of said dose rate slider.

20. The non-transitory computer-readable storage medium of claim 16, wherein said method further comprises precomputing updates to said first window corresponding to a plurality of dose rate ranges.

21. The graphical user interface of claim 1, wherein
the dose rate slider includes an indicator that is adjustable along a track,
the track includes radiation dose rates between a minimum dose rate and a maximum dose rate, and
the range of radiation dose rates is set by moving the indicator along the dose rate slider to a position associated with a first dose rate.

* * * * *